United States Patent [19]

Brammer et al.

[11] 4,303,659

[45] Dec. 1, 1981

[54] SCHISTOSOMICIDAL COMPOSITIONS

[75] Inventors: Keith W. Brammer; John R. Shaw, both of Canterbury, England

[73] Assignee: Pfizer Inc., New York, N.Y.

[21] Appl. No.: 177,687

[22] Filed: Aug. 13, 1980

[30] Foreign Application Priority Data

Aug. 22, 1979 [GB] United Kingdom ............... 29246/79

[51] Int. Cl.$^3$ .................... A61K 31/495; A61K 31/47
[52] U.S. Cl. ...................................... 424/250; 424/258
[58] Field of Search ................................ 424/250, 258

[56] References Cited

FOREIGN PATENT DOCUMENTS 1166538 10/1969 United Kingdom .
1441554 7/1976 United Kingdom .

Primary Examiner—Jerome D. Goldberg

Attorney, Agent, or Firm—Francis X. Murphy; Charles J. Knuth; Peter C. Richardson

[57] ABSTRACT

Certain novel schistosomicidal pharmaceutical compositions are disclosed. These compositions involve the concomitant use of two different organic chemical compounds each chosen from a separate class of known schistosomicidal agents. One class of agents involves certain known 2-aminoalkyl-7-substituted-1,2,3,4-tetrahydroquinolines (A), while the other class is primarily concerned with a series of known 2-acyl-4-oxo-1,2,3,6,7,11b-hexahydro-4H-pyrazino[2,1a]isoquinoline derivatives (B). A preferred embodiment involves the use of dl-6-hydroxymethyl-2-isopropylaminomethyl-7-nitro-1,2,3,4-tetrahydroquinoline (A) in conjunction with 2-cyclohexylcarbonyl-4-oxo-1,2,3,6,7,11b-hexahydro-4H-pyrazino[2,1a]isoquinoline (B). Various methods for administering these compounds in combination and/or in a concomitant manner are provided.

5 Claims, No Drawings

SCHISTOSOMICIDAL COMPOSITIONS

BACKGROUND OF THE INVENTION

This invention relates to new pharmaceutical compositions which are of therapeutic value in the treatment of schistosomiasis. More particularly, it is concerned with the concomitant use of two chemical compounds each chosen from a different group of compounds already known to be useful in the treatment of schistosomiasis, but whose concomitant use for such treatment has not been previously known.

One of the two known groups of chemical compounds is a series of 2-aminoalkyl-7-substituted-1,2,3,4-tetrahydroquinolines (A) disclosed and claimed in United Kingdom Patent Specification No. 1,166,538 and it includes the compound known as oxamniquine, which is dl-6-hydroxymethyl-2-isopropylaminomethyl-7-nitro-1,2,3,4-tetrahydroquinoline. The other known group of compounds useful in this connection involves several 2-acyl-4-oxo-1,2,3,6,7,11b-4H-pyrazino[2,1a]isoquinoline derivatives (B) that are disclosed and claimed in United Kingdom Patent Specification No. 1,441,554 and it includes the compound known as praziquantel, which is 2-cyclohexylcarbonyl-4-oxo-1,2,3,6,7,11b-hexahydro-4H-pyrazino [2,1a]isoquinoline.

SUMMARY OF THE INVENTION

According to the present invention, there are provided new schistosomicidal pharmaceutical compositions comprising a compound (A) of the formula:

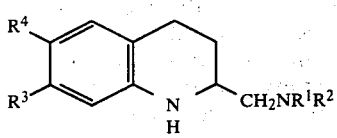

wherein $R^1$ and $R^2$ are each hydrogen, alkyl having from one to four carbon atoms, hydroxyalkyl having from one to four carbon atoms in the alkyl moiety, or cycloalkyl having from three to six carbon atoms; $R^3$ is nitro, cyano or halogen (fluorine, chlorine, bromine or iodine), and $R^4$ is methyl or hydroxymethyl; or a pharmaceutically acceptable acid addition salt thereof; and a compound (B) of the formula:

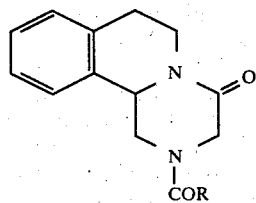

wherein R is cyclohexyl, 3-cyclohexenyl, 4-pyridyl, phenyl, 2-fluorophenyl or 4-aminophenyl, with or without a pharmaceutically acceptable carrier or diluent.

Oxamniquine is the compound (A) of formula (I) in which $R_1$ is hydrogen, $R_2$ is isopropyl, $R_3$ is nitro and $R^4$ is hydroxymethyl. Praziquantel is the compound (B) of formula (II) in which R is cyclohexyl.

Pharmaceutically acceptable acid addition salts of the compounds of the formula (I) are those which are formed with acids having pharmaceutically acceptable anions, e.g., the hydrochloride, hydrobromide, hydroiodide, sulfate or bisulfate, phosphate or acid phosphate, acetate, maleate, fumarate, lactate, tartrate, citrate, gluconate, saccharate and p-toluenesulfonate salts.

More specifically, it has been found that the concomitant use of a compound (A) of the formula (I) with a compound (B) of the formula (II) is particularly and unexpectedly valuable in the treatment of schistosomiasis. In view of this unexpected synergism, the concomitant use of these two compounds in the treatment of schistosomiasis is much more effective than the use of either compound alone.

Thus, a further aspect the present invention provides is a method of treating schistosomiasis in an animal, including a human being, which comprises administering concomitantly to the animal effective amounts of a compound (A) of the formula (I), or a pharmaceutically acceptable acid addition salt thereof, and a compound (B) of the formula (II).

Preferably, the compounds are administered orally in a ratio of about one part by weight of compound (A) of the formula (I) to about 0.5–5.0 parts by weight of compound (B) of the formula (II). The preferred weight ratio of compound (A) to compound (B) is about 1.0:2.0 for the present purposes at hand.

DETAILED DESCRIPTION OF THE INVENTION

In general, the herein described compounds (A) and (B) can be administered as schistosomicides by either the oral or parenteral routes of administration in the dose ratios (by weight) indicated above, viz., from about one part by weight of the free base of compound (A) to about 0.5–5.0 parts by weight of the free base of compound (B). In this way, they may be administered simultaneously, i.e., in single or separate tablets, capsules, syrups or other oral dosage forms, or sequentially in separate oral dosage forms. The compounds can also be administered parenterally in similar ratios, again either simultaneously or sequentially, via either single or separate parenteral dosage forms, etc.

The daily dosage levels of each of the compounds (A) and (B) will depend on the age and weight of the subject being treated, but (expressed as the free base of each compound) will generally be in the respective ranges of approximately 1–20 mg./kg. of body weight per day of compound (A) of the formula (I) and from about 2.4–40 mg./kg. of body weight per day of compound (B) of the formula (II) when administered either orally or parenterally. The preferred dosage levels are 3–10 mg./kg. of compound (A) of the formula (I) and 6–20 mg./kg. of compound (B) of the formula (II). Thus, for an average adult (70 kg.) subject, from approximately 70–1400 mg. (preferably, about 210–700 mg.) of the compound (A) of formula (I) and from approximately 175–2800 mg. (preferably, about 420–1400 mg.) of the compound (B) of formula (II) will be administered per day in either a single dose or up to four divided doses for the present purposes at hand.

Preferably, the compounds will be administered together in the form of a pharmaceutical composition comprising a compound (A) of the formula (I), or a pharmaceutically acceptable acid addition salt thereof, and a compound (B) of the formula (II), the weight ratio (expressed as the free base of each compound) of compound (A) to compound (B) being from about 1.0:0.5 up to about 1.0:5.0, respectively and the composition will usually also comprise a pharmaceutically acceptable carrier or diluent. The compositions will preferably be in a form suitable for oral administration, e.g., in the form of tablets, capsules, emulsions, syrups or elixirs, but may be in a form suitable for parenteral administration, e.g., in the form of sterile injectable solutions. Suitable compositions can contain from about 20–350 mg. of compound (A) of the formula (I) and from about 40–700 mg. of compound (B) of the formula (II), with the weight ratio of compound (A) to compound (B) being in the range of from about 1.0:0.5 to about 1.0:5.0, as aforesaid, and preferably about 1.0:2.0, respectively.

Compositions in forms suitable for either oral or parenteral administration may be prepared by methods which are well known to those skilled in the art. When the compositions are in the form of tablets or capsules, they will generally contain excipients such as starch or lactose.

The concomitant administration of compound (A) and compound (B), as described above, is especially effective in the treatment of schistosomiasis due to the Puerto Rican strain of *Schistosoma mansoni*.

EXAMPLES 1 to 3

The following ingredients are intimately mixed in the proportions given and then granulated by a conventional wet granulation technique. The resulting wet mass is dried and the dry mass screened in a conventional manner. The resulting granules are lubricated with a semi-synthetic triglyceride lubricant and filled into capsules to give a plug weight of 354 mg. per capsule.

The proportions of the ingredients are given in parts by weight.

| Example | 1 | 2 | 3 |
|---|---|---|---|
| Oxamniquine (free base) | 160 | 80 | 40 |
| Praziquantel | 80 | 160 | 200 |
| Lactose | 70 | 70 | 70 |
| Maize Starch | 40 | 40 | 40 |
| Semi-synthetic triglyceride lubricant | 4 | 4 | 4 |
|  | 354 | 354 | 354 |
| Wt. ratio oxamniquine: praziquantel | 1:0.5 | 1:2 | 1:5 |

EXAMPLES 4 to 6

The following ingredients are intimately mixed together in the proportions shown and then granulated by a conventional wet granulation technique. The resulting wet mass is dried and the dry mass is then screened in a conventional manner. The resulting granules are lubricated with a semi-synthetic triglyceride lubricant and the lubricated granules compressed into tablets of a suitable size (505 mg.). The tablets are then coated with a film of hydroxypropylmethylcellulose by a conventional technique using conventional equipment to give tablets with a final coated weight of 525 mg.

The proportions of the ingredients are given in parts by weight.

| Example | 4 | 5 | 6 |
|---|---|---|---|
| Oxamniquine (free base) | 160 | 80 | 40 |
| Praziquantel | 80 | 160 | 200 |
| Lactose | 200 | 200 | 200 |
| Maize Starch | 60 | 60 | 60 |
| Semi-synthetic triglyceride lubricant | 5 | 5 | 5 |
|  | 505 | 505 | 505 |
| Wt. ratio oxamniquine: praziquantel | 1:0.5 | 1:2 | 1:5 |

EXAMPLES 7 to 9

Suspensions suitable for oral administration are prepared with the following ingredients:

| Example | 7 | 8 | 9 |
|---|---|---|---|
| Oxamniquine (free base) | 50 g | 25 g | 12.5 g |
| Praziquantel | 25 g | 50 g | 62.5 g |
| Agar | 4 g | 4 g | 4 g |
| Sucrose | 550 g | 550 g | 550 g |
| Glycerin | 120 g | 120 g | 120 g |
| Sorbitol solution | 100 g | 100 g | 100 g |
| Sodium saccharin | 1 g | 1 g | 1 g |
| Sodium chloride | 10 g | 10 g | 10 g |
| "Polysorbate 80" (wetting agent) | 1 g | 1 g | 1 g |
| Flavorings | 2 g | 2 g | 2 g |
| Purified water | to 1 liter | | |
| Wt. ratio oxamniquine: praziquantel | 1:0.5 | 1:2 | 1:5 |

The suspensions are prepared by dissolving the Polysorbate 80 (polyoxyethylene sorbitan mono-oleate) in purified water and adding praziquantel and oxamniquine, which are dispersed well. An agar solution is prepared by heating to boiling, followed by addition of the glycerin, sorbitol solution, sucrose, sodium saccharin and sodium chloride. The resulting solution is then cooled and added to the Polysorbate 80/praziquantel/oxamniquine solution, followed by the addition of the flavorings and making up to a 1 liter volume. The suspensions are then filled into bottles of a suitable size (100 ml.), each 5 ml. dose of which contains 375 mg. of active ingredient.

EXAMPLE 10

The effectiveness of the method and compositions of the invention in the treatment of schistosomiasis has been assessed using a Puerto Rican strain of *Schistosoma mansoni* maintained by serial passage through Charles River (UK) CD-1 female albino mice and *Biomphalaria glabrata* snails. Male mice are infected with 100 cercariae of *Schistosoma mansoni* and used 8–10 weeks post infection. The test compound(s) are suspended (at the desired concentration level) in a 10% solution of Cremophor EL in 0.2 M phosphate buffer at pH 7.0 (Cremophor EL is the registered trademark name of Badische Anilin und Soda-Fabrik of Ludwigshafen, West Germany for glycerol-polyethylene glycol-ricinoleate). When both oxamniquine and praziquantel are to be administered in combination, they are first individually suspended in the buffered system described above and the two suspensions are then mixed together immediately before use.

The resulting mixture is then administered to the mice by an oral gavage needle, using 0.3 ml. of the above suspension for a 30-gram animal. Fourteen days post treatment, the mice are killed by cervical dislocation and living worms are recovered from the blood vessels by perfusion. The liver is then removed and compressed between two glass plates, and the encapsulated (i.e., dead) worms are counted.

Effective doses required to kill 50% and 99% of male worms (i.e., $ED_{50}$ and $ED_{99}$ values, respectively) are calculated from the regression line of the dose response data.

| Compound | $ED_{50}$ (mg./kg.) | $ED_{99}$ (mg./kg.) |
| --- | --- | --- |
| Oxamniquine alone | 39.0 | 89.0 |
| Oxamniquine in combination with 25 mg./kg. of praziquantel | 8.6 | 16.6 |
| Praziquantel alone | 156.0 | 296.0 |
| Praziquantel in combination with 12.5 mg./kg. of oxamniquine | 4.9 | 27.2 |

Thus, it is seen that the total dose required for the combination to achieve equal efficacy to individual compound treatments at the $ED_{99}$ level is about one-half the dose using oxamniquine alone or one-seventh the dose using praziquantel alone. Also, a combination treatment using a 4–5 fold decrease in oxamniquine with an 8–10 fold decrease in praziquantel is as effective as individual treatments at the $ED_{99}$ level. The most effective combination in mice is the mixture involving about one part by weight of oxamniquine with two parts by weight of praziquantel. These results indicate an unexpected synergistic effect between oxamniquine and praziquantel.

We claim:

1. A schistosomicidal composition comprising a compound (A) which is dl-6-hydroxymethyl-2-isopropylaminomethyl-7-nitro-1,2,3,4-tetrahydroquinoline or a pharmaceutically acceptable acid addition salt thereof and a compound (B) which is 2-cyclohexylcarbonyl-4-oxo-1,2,3,6,7,11b-hexahydro-4H-pyrazino[2,1a]isoquinoline wherein the weight ratio of the free base of compound (A) to the free base of compound (B) is in the range of from about 1.0:0.5 up to about 1.0:5.0.

2. A composition as claimed in claim 1 wherein the weight ratio of (A) to (B) is about 1.0:2.0.

3. A schistosomicidal pharmaceutical composition comprising an effective schistosomicidal amount of the composition as claimed in claim 1 and a pharmaceutically acceptable carrier.

4. A method for treating schistosomiasis in an afflicted animal, which comprises administering concomitantly to said animal an effective schistosomicidal amount of the schistosomicidal composition of claim 1.

5. A method as claimed in claim 4 wherein the compounds are administered orally.

* * * * *